(12) United States Patent
Kuo

(10) Patent No.: US 10,022,414 B2
(45) Date of Patent: Jul. 17, 2018

(54) MULTI-CAROTENOIDS COMPOSITIONS AND METHODS

(75) Inventor: Fu Feng Kuo, Richmond (CA)

(73) Assignee: Health Ever Bio-Tech Co., Ltd., Taipei (TW)

( * ) Notice: Subject to any disclaimer, the term of this patent is extended or adjusted under 35 U.S.C. 154(b) by 811 days.

(21) Appl. No.: 12/545,287

(22) Filed: Aug. 21, 2009

(65) Prior Publication Data

US 2009/0312287 A1   Dec. 17, 2009

Related U.S. Application Data

(63) Continuation-in-part of application No. 11/695,354, filed on Apr. 2, 2007, now abandoned.

(30) Foreign Application Priority Data

Apr. 3, 2006   (TW) .............................. 095111722 A

(51) Int. Cl.

| | |
|---|---|
| *A61K 36/81* | (2006.01) |
| *A61K 9/48* | (2006.01) |
| *A61K 31/01* | (2006.01) |
| *A61K 31/015* | (2006.01) |
| *A61K 31/355* | (2006.01) |
| *A61K 31/56* | (2006.01) |
| *A61K 31/685* | (2006.01) |
| *A61K 36/42* | (2006.01) |
| *A61K 36/48* | (2006.01) |
| *A61K 36/87* | (2006.01) |
| *A23L 5/44* | (2016.01) |
| *A23L 33/105* | (2016.01) |
| *A23L 33/11* | (2016.01) |

(52) U.S. Cl.
CPC ............... *A61K 36/81* (2013.01); *A23L 5/44* (2016.08); *A23L 33/105* (2016.08); *A23L 33/11* (2016.08); *A61K 9/4875* (2013.01); *A61K 31/01* (2013.01); *A61K 31/015* (2013.01); *A61K 31/355* (2013.01); *A61K 31/56* (2013.01); *A61K 31/685* (2013.01); *A61K 36/42* (2013.01); *A61K 36/48* (2013.01); *A61K 36/87* (2013.01)

(58) Field of Classification Search
None
See application file for complete search history.

(56) References Cited

U.S. PATENT DOCUMENTS

| | | | | |
|---|---|---|---|---|
| 4,316,917 | A | * | 2/1982 | Antoshkiw et al. .......... 426/540 |
| 6,132,790 | A | * | 10/2000 | Schlipalius .................... 426/540 |
| 2003/0104078 | A1 | * | 6/2003 | Barrett-Reis ........... A23L 33/15 424/727 |
| 2005/0031557 | A1 | | 2/2005 | Gaertner |
| 2006/0009430 | A1 | | 1/2006 | Kelly |

FOREIGN PATENT DOCUMENTS

| | | |
|---|---|---|
| CN | 1327749 A | 12/2001 |
| CN | 1343518 A | 4/2002 |
| CN | 1352939 A | 6/2002 |
| CN | 1352940 A | 6/2002 |
| CN | 1413590 A | 4/2003 |
| CN | 1736396 A | 2/2006 |
| JP | H10226654 A | 8/1998 |
| JP | 2002125619 A | 5/2002 |
| WO | WO 02/058683 A2 * | 8/2002 |
| WO | 2004052351 A1 | 6/2004 |

OTHER PUBLICATIONS

Karmanos (2001, https://www.karmanos.org/view_news.asp?id=104).
E Kotake-Nara et al. Carotenoids Affect Proliferation of Human Prostate Cancer Cells. J Nutr. Dec. 2001, 3303-3306, 131(12).
O Kucuk et al. Effects of lycopene supplementation in patients with localized prostate cancer. Experimental Biology and Medicine, 2002, 881-885, 227.
E Giovannucci. A Review of Epidemiologic Studies of Tomatoes, Lycopene, and Prostate Cancer. Experimental Biology and Medicine, 2002, 852-859, 227.
JK Campbell et al. Biosynthesis of 14C-Phytoene from Tomato Cell Suspension Cultures (Lycopersicon esculentum) for Utilization in Prostate Cancer Cell Culture Studies. J. Agric Food Chem, 2006 8;(54)3:747-755.
Canadian Office Action for Canadian Patent Application No. 2,583,658, dated Nov. 26, 2013.
US Office Action for U.S. Appl. No. 12/479,094, dated Dec. 13, 2013.
Kucuk et al., Cancer Epidemiology, Biomarkers & Prevention, 2001, 861-868, 10.

* cited by examiner

*Primary Examiner* — Terry A McKelvey
*Assistant Examiner* — Catheryne Chen
(74) *Attorney, Agent, or Firm* — Young & Thompson

(57) ABSTRACT

A stable nutritional supplement composition for oral administration comprising, in one form, about 71% by weight, of a tomato extract containing therein at least 2% to 10% by weight of lycopene, 0.25% to 2% by weight of phytoene, and 0.2% to 2% by weight of phytofluene, and about 29% by weight, of a suitable encapsulating matrix. A suitable encapsulating matrix is an edible oil exemplified by soya oil, pumpkin seed oil, grape-seed oil and the like. The tomato extract may additionally comprise one or more of at least one carotene selected from the group comprising .beta.-carotene, .gamma.-carotene, and .delta.-carotene, a phytosterol, a tocopheral and a phospholipid. The tomato extract may be further processed into oleoresin emulsions, or into beadlets, or into dry powders. Methods for ameliorating the effects of aging-related urinary tract malfunctions in men, comprising orally administrating on a regular basis, an effective amount of the nutritional supplement compositions disclosed herein.

13 Claims, No Drawings

MULTI-CAROTENOIDS COMPOSITIONS AND METHODS

This application is a continuation in part of co-pending Ser. No. 11/695,354 filed Apr. 2, 2007 (Title: MULTI-CAROTENOIDS COMPOSITIONS AND USES THEREFOR), with Ser. No. 12/479,094 filed on Jun. 5, 2009 (Title: MULTI-CAROTENOIDS COMPOSITIONS AND USES THEREFOR), a division of Ser. No. 11/695,354 filed Apr. 2, 2007, and claims priority from Taiwan Patent Application Serial No. 095111722, filed Apr. 3, 2006.

TECHNICAL FIELD

This invention relates to compositions comprising a plurality of carotenoid compounds. More particularly, the present invention is directed to nutritional supplement compositions comprising at least lycopene, phytoene and phytofluene, configured for oral administration as a nutritional supplement. The present invention also relates to methods for use of said compositions disclosed herein.

BACKGROUND OF THE INVENTION

Carotenoids are a group of pigments that are characterized by the color including and ranging from yellow to red. Carotenoids are commonly produced by a wide variety of plant materials and most commonly associated with plants such as tomatoes, carrots and peppers.

Lycopene and its precursor phytofluene are carotenoids commonly found in tomatoes and are the predominant sources of the bright red color associated with tomatoes. Phytoene is a precursor to phytofluene, lycopene and other carotenoids, and is also found in high concentrations in tomatoes. Lycopene is generally present in the plasma of the human body; the serum concentrations of lycopene are typically about 2.5 times higher than those of .alpha.-carotene and 7.5 times greater than those of .beta.-carotene. Carotenoids are known to have antioxidant properties and consequently, provide numerous beneficial health effects including reducing the potential risks of cardiovascular diseases, cancers, and slowing and/or reversing the degenerative effects of aging on various human physiological activities.

Prostate cancer and benign prostatic hyperplasia (also called BPH) are aging-related conditions that affect prostate gland physiology and impair urinary function in men. As many men age, their prostate glands slowly enlarge causing (a) obstructive symptoms exemplified by weak and/or intermittent urinary streams, a sense of residual urine in the bladder after voiding, and dribbling or leakage at the end of urination, and/or (b) irritative symptoms as exemplified by urgency of micturation, increased frequency of urination, and uracratia. Obstructive and irritative urinary symptoms are commonly referred to as lower urinary tract symptoms (LUTS). The current treatments of prostrate cancer, BPH and LUTS symptoms consist of drug therapies and major surgery. The two primary drug classes used are alpha-blockers and 5-alpha-reductase inhibitors, which should be taken for life in order to get the persistent efficacy. When surgery is considered, the results are usually positive, but there are risks associated with such surgical operations.

US Patent Publication 2005/0031557 describes an oral composition containing lutein, phytoene and phytofluene, but professing no preference for any specific amount of either of phytoene or phytofluene relative to lutein or any one of the list consisting of .alpha.-carotene, astaxanthin, .alpha.-cryptoxanthin, .beta.-cryptoxanthin, zeaxanthin, phytoene, phtyofluene, .gamma.-carotene and neurosporin, nor any especially important reason for including any of the members of that list in the composition. The '557 publication fails to indicate any important benefit may be obtained by inclusion of phytoene or phytofluene in the composition relative to any other component thereof.

SUMMARY OF THE INVENTION

The exemplary embodiments of the present invention, at least in preferred forms, are directed to stable multi-carotenoids compositions useful for oral administration as nutritional supplements, wherein the compositions comprise at least lycopene, phytoene, phytofluene components, and a suitable carrier.

According to one aspect, the lycopene, phytoene, and phytofluene components of the multi-carotenoid compositions of the present invention are preferably naturally occurring and are preferably extracted from tomatoes as pulp. The tomato pulp is suitably processed into oleoresins or beadlet or dry powder materials. The multi-carotenoid compositions of the present invention comprise said oleoresin, or beadlet, or dry powder materials, are suitably encapsulated in soft-gel capsules, or alternatively, in "hard" capsules, or optionally, configured into tablets, or if so desired, into sachet packets, and like.

According to another aspect, the tomato extracts comprising the multi-carotenoids compositions of the present invention may additionally contain therein addition to the lycopene, phytoene, and phytofluene components, one or more of .beta.-carotene, .gamma.-carotene, and .delta.-carotene, a phytosterol, a tocopheral and a phospholipid. An exemplary formulation of the multi-carotenoids compositions, comprises lycopene, phytoene, phytofluene, and vitamin E components with trace amounts of .beta.-carotene, .gamma.-carotene, and .delta.-carotene, within a tomato oil matrix encased in a soft gel capsule. The exemplary formulation may additionally comprise an edible oil exemplified by soya oil, pumpkin seed oil, grapeseed oil and the like.

According to another embodiment of the present invention, there are provided methods for regular oral administration of the multi-carotenoids compositions disclosed herein thereby regularly providing an effective amount of lycopene useful for ameliorating the effects of aging-related urinary impairments and malfunctions in men. Such urinary impairments and malfunctions are exemplified by benign prostatic hyperplasia, prostate cancer, lower urinary tract symptoms such as obstructive symptoms and irritative symptoms, and the like.

DETAILED DESCRIPTION OF THE INVENTION

The present invention provides stable multi-carotenoids compositions useful for oral administration as nutritional supplements, wherein the compositions comprise at least lycopene, phytoene, phytofluene components contained within an extract produced from tomato fruits. Suitable tomato fruits are produced by non-genetically engineered plants, and preferably contain high concentrations of lycopene. The compositions are preferably encased in a soft gel capsule and may additionally comprise an edible oil exemplified by soya oil, pumpkin seed oil, grapeseed oil and the like.

The lycopene, phytoene and phytofluene components are preferably processed from tomato fruits into extracts. The components may be concentrated by removing water from the extracts thereby producing thickened pulps that contain therein the lycopene, phytoene and phytofluene components, and additionally comprise .beta.-carotene, .gamma.-carotene, .delta.-carotene, vitamin E, a plurality of phytosterols and phospholipids. The thickened pulps may be further suitably processed into oleoresin-based emulsions. The oleoresins may be encapsulated within soft gel capsules comprising soya oil or alternatively, pumpkin seed oil. The tomato extracts may be optionally formulated into beadlets that may be packaged if so desired in sachet packets, or alternatively, dried and processed into powders that may be optionally encapsulated or alternatively, tableted.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The nutritional formulas and corresponding methods of the present invention can comprise, consist of, or consist essentially of the essential elements and limitations of the invention described herein, as well as any additional or optional ingredients, components, or limitations described herein or otherwise useful in nutritional formula applications.

One form of the multi-carotenoids composition of the present invention is a soft gel capsule configured for oral administration as a nutritional supplement and comprises about: (a) 71% by weight of a tomato extract containing about 2% to 10% by weight of lycopene, 0.25% to 2% by weight of phytoene, 0.2% to 2% by weight of phytofluene, trace amounts of carotene, .beta.-carotene, .gamma.-carotene, .delta.-carotene, vitamin E, phytosterols and phospholipids, and (b) 29% weight of a suitable encapsulating matrix exemplified by soya oil or pumpkin seed oil. An exemplary multi-carotenoids composition is a soft gel capsule weighing about 350 mg and comprising firstly, about 250 mg of a tomato oleoresin containing: (a) about 15 mg of lycopene, (b) about 1.5 mg of phytoene, (c) 1.25 mg of phytofluene, (d) about 5 mg of vitamin E, (e) about 0.5 mg of .beta.-carotene, (f) about 1.5 mg of a phytosterol, and (g) 25 mg of a phospholipid, and secondly, about 100 mg of soya oil or alternatively, about 100 mg of pumpkin seed oil and the like.

Non-limiting examples of a preferred source of lycopene, phytoene, and phytofluene or combinations thereof in the invention composition include an oleoresin product of tomato extract known as Lyc-O-Mato® in liquid, oil-dispersible form and provided by LycoRed Ltd., Bear Sheba, Israel, pursuant to their process for recovering a lycopene-rich oleoresin from tomato pulp under U.S. Pat. No. 5,837,311, which incorporated by reference herein.

Method of Manufacture

The multi-carotenoids composition of the present invention may be prepared by any known or otherwise effective technique suitable for making and formulating a nutritional formula or similar other formula, variations of which may depend upon variables such as the selected product form, ingredient combination, packaging and container selection, and so forth, for the desired formula. Such techniques and variations for any given formula are easily determined and applied by one of ordinary skill in the nutritional formulation or manufacturing arts.

The multi-carotenoids composition of the present invention, including the exemplified formulas described herein, can therefore be prepared by any of a variety of known or otherwise effective formulation or manufacturing methods with present disclosures.

These methods most typically involve the initial obtaining of an essentially pulp-free tomato extract of the above Lyc-O-Mato® and subsequent dilution by way of edible oils with a resulting desired concentration of lycopene, phytoene, and phytofluene in a mixture essentially free of lutein. Further, as used herein, "essentially consisting of" means that the multi-carotenoids composition of the present invention contains other components than those specifically identified but are of negligible or neutral effect with respect to the objects of the invention. Thus, it is well known that the pulp-free tomato extract of Lyc-O-Mato® may contain many components other than those specifically identified in the multi-carotenoids composition of the present invention, said tomato extract contains essentially no other components affecting the objects of this invention. Various other solutions, mixtures, or other materials may be added to the resulting desired diluted tomato extract before, during, or after further processing. The diluted tomato extract can, in addition to being made into soft gel capsules, then be further diluted, heat-treated, and packaged to form a ready-to-eat or concentrated liquid, or it can be heat-treated and subsequently processed and packaged as a reconstitutable powder, e.g., spray dried, dry mixed, agglomerated.

The present inventor has found that phytoene and phytofluene in the specific ratios identified herein to each other and to lycopene to be critical to the objects of the invention, i.e., to cooperatively influence the course of human disease processes as described herein. Further, the present inventor selected the above described tomato extract composition (such as an oleoresin) resulting in a high concentration of lycopene:phytofluene:phytoene specifically to be mixed with and diluted by one or more of the identified edible oils as critical to the bioavailability to a user for influencing the course of BPH by the multi-carotenoids composition of the present invention. The prior art does not describe an essentially lutein-free, multi-carotenoids composition of the present invention diluted to effective strength as in the present invention. The oleoresin of the '311 patent is available in lycopene concentrations of from 4 to 20 percent. The multi-carotenoids composition of the present invention is preferably from 2 to 10 percent lycopene, necessitating dilution by essential edible oils of said oleoresin by about 50 percent or as appropriate. Dilution by specific edible oils by at least 10 percent, and more preferably 20 percent, of a concentrate of the multi-carotenoids of the invention is critical to their bioavailability to an ingesting user.

The requisite use of phytoene and phytofluene with lycopene in the multi-carotenoids composition of the present invention to obtain the objects of the invention has not before been realized in the prior art, particularly because those two components have not been known in the art of BPH amelioration to be available independent of complex mixtures of organic molecules in various plant extracts, which introduce unacceptable amounts of other such molecules. The present inventor has found in U.S. Pat. No. 7,482,032, which is incorporated herein, that phytoene and phytofluene are available in substantial quantities for use in the invention composition as an extract from an algal source at about 50 mg/l of culture material or higher by way of further extraction. The method manufacture of the invention composition thus includes obtaining lycopene from a suitable source consisting essentially of lycopene and adding to it phytoene and phytofluene sufficient to meet the requirements of the specific ratios described herein of those two components to lycopene.

Human Clinical Study Results

A 12-week clinical study was initiated with a group of 74 males recruited and randomized into two sub-groups of 37 individuals each, to assess the effects of an exemplary capsule formulation of the multi-carotenoids composition of the present invention. Twelve individuals were subsequently withdrawn from the study due to screening failure, and the remaining 62 subjects were: (a) a first group of 29 subjects who received a daily oral dose of one 350-mg capsule of the exemplary capsule of the present invention thereby providing a daily nutritional supplement of 15 mg of lycopene, and (b) a second group of 33 subjects who received a daily oral dose of two 350-mg capsules of the present invention thereby providing a daily nutritional supplement of 30 mg of lycopene, on selected clinical parameters associated with prostate and urinary system health. The inclusion criteria for the trial were male subjects over 40 years of age with no prior history or indicators of prostate and/or other cancers, the subjects' PSA levels were between 2.5 and 20.0 ng/ml, and their renal and liver functions were within normal ranges. The exclusion criteria were individuals with fluctuating PSA levels, recent medical histories of urinary tract infection, prostatitis, acute urinary retention, individuals with known allergic reactions to carotenoids, individuals taking medications that may alter serum PSA levels as exemplified by 5-.alpha. reductase inhibitors, steroids or hormonal agents, and medications for lower urinary tract infections.

The trial followed a general protocol of, first, screening, evaluation and selection of the individuals for participating in the trial. Second, a 2-week washout period was undertaken during which the individuals maintained their normal lifestyle and eating habits while avoiding all lycopene foods such as tomato products, guava, pink grapefruits and the like. Third, at the end of the 2-week washout period, each individual's serum was sampled (i.e., the first sample) after which, they were assigned to one of the two lycopene dosage groups. Fourth, the individuals in each group received their daily dosage for 12 consecutive weeks. Each individual's serum was sampled after one week (i.e., the second sample), after four weeks (i.e., the third sample) and after twelve weeks (i.e., the fourth sample). Each serum sample was assayed to quantitatively determine therein the PSA, lycopene, creatine, bilirubin, alanine amino transferase, hemoglobin, cholesterol, low-density lipoprotein, high-density lipoprotein, and testosterone levels. At each sampling time, the test individuals were also responded to questions regarding their urinary functions taken from the International Prostate Symptom Score (IPSS) index developed and validated by a multidisciplinary measurement committee of the American Urological Association (Fowler et al., 1992, Journal of Urology 148:1549-57).

The time "0" data (i.e., the first sample) are shown in Table 1. Individuals receiving a daily lycopene dose of 15 mg via one capsule daily of the exemplary composition of the present invention showed a 2.6 times increase in their serum lycopene levels, while individuals receiving a daily lycopene dose of 30 mg via two capsules daily showed a 3-fold increase in their serum lycopene levels (Table 2).

TABLE 1

Summary of test individual baseline data at the first sample time (0 time)*

| Parameter | Lycopene dosage 15 mg/day | Lycopene dosage 30 mg/day | |
|---|---|---|---|
| Age (years) | 63.4 ± 8.1 | 63.9 ± 9.7 | P = 0.9 |
| Median PSA (ng/mL) | 8.8 ± 4.2 | 7.8 ± 3.8 | P = 0.3 |
| Median PSA range (ng/mL) | 3.5-18.4 | 2.7-17.5 | |
| IPSS | 11.3 ± 5.8 | 12.3 ± 6.5 | P = 0.5 |
| Body mass index | 24.6 ± 2.0 | 24.2 ± 2.9 | P = 0.9 |
| Serum total lycopene (ng/mL) | 297.9 ± 127. | 303.0 ± 162. | P = 0.9 |
| Serum creatine (mg/dL) | 1.07 ± 0.15 | 1.14 ± 0.15 | P = 0.06 |
| Serum bilirubin (mg/dL) | 0.9 ± 0.3 | 0.9 ± 0.3 | P = 0.4 |
| Alanine amino transferase (U/L) | 21.6 ± 7.9 | 18.5 ± 6.3 | P = 0.08 |
| Serum hemoglobin (mg/dL) | 14.4 ± 1.0 | 14.6 ± 1.2 | P = 0.5 |
| Serum cholesterol (mg/dL) | 198.4 ± 33.7 | 205.9 ± 32.5 | P = 0.4 |
| Low-density lipoprotein (mg/dL) | 122.5 ± 28.2 | 132.1 ± 54.9 | P = 0.4 |
| High-density lipoprotein (mg/dL) | 41.5 ± 9.2 | 44.2 ± 10.3 | P = 0.3 |
| Serum triglycerides (mg/dL) | 122.6 ± 53.1 | 115.6 ± 68.4 | P = 0.7 |
| Serum testosterone (mg/dL) | 4.5 ± 1.7 | 4.8 ± 1.9 | P = 0.5 |

*Data are means ± standard deviations

TABLE 2

Changes in serum lycopene levels after 12 weeks of supplementation with the exemplary composition of the present invention*.

| Sample time | Lycopene dosage 15 mg/day | Lycopene dosage 30 mg/day | |
|---|---|---|---|
| Time "0" (baseline) | 279.9 ± 127.3 | 303.0 ± 162.3 | P = 0.9 |
| After 12 weeks | 780.0 ± 224.1 | 947.5 ± 290.4 | P = 0.01 |

*Serum lycopene levels are reported as ng./mL means ± standard deviations.

The median results indicated that the test individuals from both daily dosage groups showed marginal declines in their PSA levels over the 12-week study (Table 3). However, a sub-group of 23 test individuals with baseline PSA levels greater than 8.0 at the first sampling time (i.e., time "0"), from both treatment groups, showed significant decreases in their PSA levels over the 12-week study (Table 4).

TABLE 3

Changes in PSA levels during 12 weeks of supplementation with the exemplary composition of the present invention*.

| | Lycopene dosage | |
|---|---|---|
| Sample time | 15 mg/day | 30 mg/day |
| Time "0" (baseline) | 8.8 ± 4.2 | 7.8 ± 3.7 |
| After 4 weeks | 8.3 ± 3.9 | 7.0 ± 3.8 |
| % change from baseline | −4% | −9% |
| | $P = 0.08$ | $P = 0.01$ |
| After 12 weeks | 8.0 ± 3.8 | 7.5 ± 4.0 |
| % change from baseline | −5.2% | −3.1% |
| | $P = 0.17$ | $P = 0.22$ |

*PSA data are reported as ng/mL means ± standard deviations.

TABLE 4

Changes in PSA levels in test individuals with elevated baseline PSAs, during 12 weeks of supplementation with the exemplary composition of the present invention.

| Sample time | PSA level (ng · mL) |
|---|---|
| Time "0" (baseline) | 12.4 ± 3.2 |
| After 4 weeks | 11.2 ± 4.1 |
| % change from baseline | −11% |
| | $P = 0.01$ |
| After 12 weeks | 10.9 ± 4.0 |
| % change from baseline | −12% |
| | $P = 0.04$ |

The test individuals from both daily dosage groups showed a progressive decline in their IPSS indices over the 12-week study (Table 5).

TABLE 5

Changes in test individuals' IPSS indices during 12 weeks of supplementation with the exemplary composition of the present invention*.

| | Lycopene dosage | |
|---|---|---|
| Sample time | 15 mg/day | 30 mg/day |
| Time "0" (baseline) | 11.3 ± 5.8 | 12.3 ± 6.5 |
| After 4 weeks | 9.5 ± 5.0 | 9.0 ± 5.0 |
| % change from baseline | −14% | −24% |
| | $P = 0.002$ | $P < 0.001$ |
| After 12 weeks | 9.1 ± 5.9 | 7.5 ± 4.0 |
| % change from baseline | −17% | −32% |
| | $P = 0.012$ | $P < 0.001$ |

*IPSS data are reported as points means ± standard deviations.

Furthermore, the test individuals from both daily dosage groups showed progressive declines in their obstructive IPSS scores and their irritative IPSS scores over the 12-week study (Table 6).

TABLE 6

Changes in obstructive and irritative IPSS scores during 12 weeks of supplementation with the exemplary composition of the present invention*.

| | Lycopene dosage | |
|---|---|---|
| Sample time | 15 mg/day | 30 mg/day |
| | Obstructive IPSS Scores* | |
| Time "0" (baseline) | 5.6 ± 3.7 | 6.9 ± 4.8 |
| After 4 weeks | 4.7 ± 2.9 | 4.9 ± 3.5 |
| % change from baseline | −0.4% | −22% |
| | $P = 0.04$ | $P < 0.001$ |
| After 12 weeks | 4.7 ± 3.7 | 4.0 ± 3.7 |
| % change from baseline | −3.4% | −27% |
| | $P = 0.18$ | $P < 0.001$ |
| | Irritative IPSS Scores* | |
| Time "0" (baseline) | 5.7 ± 3.0 | 5.4 ± 2.9 |
| After 4 weeks | 4.9 ± 2.7 | 4.1 ± 2.2 |
| % change from baseline | −11% | −16% |
| | $P = 0.009$ | $P < 0.001$ |
| After 12 weeks | 4.4 ± 2.5 | 3.6 ± 2.0 |
| % change from baseline | −16% | −27% |
| | $P = 0.001$ | $P < 0.001$ |

*Obstructive and irritative IPSS data are reported as score means ± standard deviations.

The exemplary embodiments of the present invention comprising multi-carotenoids nutritional supplement compositions as disclosed herein for provision of a daily nutritional supplement of at least 15 mg of lycopene, are useful for ameliorating the effects of aging-related impaired urinary functions in men as exemplified by BPH, LUTS, prostrate cancer and the like.

It has been found that .alpha.-tocopherol exerts an additional complementary and multiplicative effect on ameliorating the effects of aging-related impaired urinary functions in men in the invention composition, especially if the .alpha.-tocopherol consists entirely of non-synthetic d,d,d-.alpha.-tocopherol in an amount less than 4 weight percent in the invention composition finally diluted with an edible oil to enhance bio-availability of the effective components of the invention composition.

While particular exemplary embodiments of the present invention have been described in the foregoing, it is to be understood that other embodiments are possible within the scope of the present invention and are intended to be included herein. In view of numerous changes and variations that will be apparent to persons skilled in the art, the scope of the present invention is to be considered limited solely by the appended claims.

I claim:

1. A composition, comprising:
   2% to 10%, by weight, based on the total weight of the composition, of lycopene;
   0.25% to 2%, by weight, based on the total weight of the composition, of phytoene;
   0.2% to 2%, by weight, based on the total weight of the composition, of phytofluene;
   α-tocopherol; and
   at least 10%, by weight, based on the total weight of the composition, of an edible oil.

2. The composition of claim 1,
   wherein said composition is essentially free of lutein.

3. The composition of claim 1, further comprising:
   at least one carotene selected from the group consisting of: β-carotene, γ-carotene; and β-carotene;
   a phytosterol; and
   a phospholipid.

4. The composition of claim 1,
wherein said α-tocopherol is non-synthetic d,d,d-α-tocopherol.

5. The composition of claim 4,
wherein said non-synthetic d,d,d-α-tocopherol is present at a level of less than 4% by weight, based on the total weight of the composition.

6. The composition of claim 1,
wherein said edible oil is selected from the group consisting of soya oil, pumpkin seed oil, and grape-seed oil.

7. A composition, comprising:
71%, by weight, based on the total weight of the composition, of a tomato extract, comprising:
  2% to 10%, by weight, based on the total weight of the composition, of lycopene;
  0.25% to 2%, by weight, based on the total weight of the composition, of phytoene;
  0.2% to 2%, by weight, based on the total weight of the composition, of phytofluene;
  α-tocopherol; and
at least 10% by weight, based on the total weight of the composition, of an edible oil.

8. The composition of claim 7,
wherein said edible oil is selected from the group consisting of soya oil, pumpkin seed oil, and grape-seed oil.

9. The composition of claim 7, further comprising:
at least one carotene selected from the group consisting of: β-carotene, γ-carotene; and β-carotene;
a phytosterol;
and
a phospholipid.

10. A soft gel capsule, comprising:
the composition of claim 1.

11. A soft gel capsule, comprising:
the composition of claim 3.

12. A soft gel capsule, comprising:
the composition of claim 3;
wherein said lycopene is present at a level of about 15 mg;
wherein said phytoene is present at a level of about 1.5 g;
wherein said phytofluene is present at a level of 1.25 mg;
wherein said carotene is β-carotene and is present at a level of about 0.5 mg;
wherein said phytosterol is present at a level of about 1.5 mg;
wherein said tocopherol is present at a level of about 5 mg; and
wherein said phospholipid is present at a level of 25 mg.

13. A soft gel capsule comprising:
the composition of claim 7.

* * * * *